United States Patent [19]

Olive et al.

[11] Patent Number: 5,052,399
[45] Date of Patent: Oct. 1, 1991

[54] HOLTER FUNCTION DATA ENCODER FOR IMPLANTABLE DEVICE

[75] Inventors: Arthur L. Olive, Stacey; William C. Lincoln, Coon Rapids, both of Minn.

[73] Assignee: Cardiac Pacemakers, Inc., St. Paul, Minn.

[21] Appl. No.: 585,509

[22] Filed: Sep. 20, 1990

[51] Int. Cl.[5] ............................................. A61B 5/0452
[52] U.S. Cl. ................................. 128/703; 364/413.06
[58] Field of Search ............... 128/696, 702, 703, 706; 364/413.05, 413.06

[56] References Cited

U.S. PATENT DOCUMENTS

| | | | |
|---|---|---|---|
| 3,518,983 | 7/1970 | Jorgensen | 128/702 |
| 3,699,949 | 10/1972 | O'Hanlon, Jr. et al. | 128/706 |
| 4,248,244 | 2/1981 | Charnitski et al. | 128/706 |
| 4,250,888 | 2/1981 | Grosskopf | 128/702 |
| 4,417,306 | 11/1983 | Citron et al. | 128/703 |
| 4,449,536 | 5/1984 | Weaver | 128/696 |

Primary Examiner—William E. Kamm
Attorney, Agent, or Firm—Fleit, Jacobson, Cohn, Price, Holman & Stern

[57] ABSTRACT

A encoding/decoding algorithm for storing cardiac cycle length data in a memory of a body implantable device. The data encoding is based on a Holter function for sequentially storing in addresses in memory data representative of cardiac cycle length intervals and data representative of changes in the cardiac cycle length intervals. The sequence of storing is dictated by the value of the time interval change data. If the value of the time interval change data is greater than the storage capacity of a single memory location, then the time interval data is stored in memory at two consecutive memory locations. On the other hand, if the magnitude of the timer interval data is within the storage capacity of a single memory cell, it is stored in memory at a single memory cell. When decoding the stored data, retrieval proceeds through the memory according to the value of the data stored so that the time interval data is reconstructed from the originally stored time interval data or change in time interval data.

19 Claims, 5 Drawing Sheets

HOLTER FUNCTION DATA ENCODER FOR IMPLANTABLE DEVICE

BACKGROUND OF THE INVENTION

The present invention relates to a data encoder, and more particularly to a data encoder for an implantable device such as a cardiac pacemaker or defibrillator.

A critical limitation of implantable devices is size or space. Electrical components which perform various functions are required to be as small and as energy efficient as possible. As a result, there is a continuing effort to design electrical systems which can perform with desired functions using the least amount of electrical energy and being as small as possible to facilitate implantation.

Specifically, when electrically storing data in and obtained by implantable circuitry, it is necessary to employ a memory device which is as compact as possible but still provides for adequate data storage and resolution for later retrieval and processing. One way to compensate for smaller memories is to encode the data prior to storage in such a way so as to require less memory space than would be necessary for the unencoded data.

SUMMARY OF THE INVENTION

It is a primary object of the present invention to provide a method for encoding data for storage in an implantable device for increasing the storage capacity of a memory in the implanted device.

It is a primary object of the present invention to provide a method and apparatus for efficiently storing data in memory in an implantable device.

It is another object of the present invention to provide a method for encoding data obtained by an implantable device prior to storage in a memory, and a method for decoding the stored data for later processing.

It is yet another object of the present invention to provide a method for storing in memory, data representative of cardiac cycle length intervals and data representative of changes in the cardiac cycle length intervals.

The data encoding method according to the present invention is based on a Holter function for sequentially storing at addresses in memory data representative of cardiac cycle length intervals and data representative of changes in the cardiac cycle length intervals. The sequence of storing is dictated by the value of the time interval and time interval change data. A time interval counter is provided in the implantable device for measuring the time interval between consecutive cardiac cycles. The time interval data is then supplied to an encoder which computes the changes between successive measures of the time interval and sequentially stores the time interval data or the change in time interval data in addresses in a memory depending on the value of the difference between successive cardiac time intervals.

When decoding the stored data, retrieval proceeds through the memory according to the value of the data stored so that the time interval data, which is what is desired to be retrieved, is reconstructed from the originally stored time interval data or change in time interval data.

In an effort to conserve space in a memory of an implantable device, the encoding algorithm according to the present invention is designed to store either data representing cardiac time interval or data representing change in cardiac time intervals. Each memory location in the memory is capable of storing a predetermined number of bits of data, for example, eight bits. Thus, the corresponding decimal equivalent of the largest binary number capable of being stored in a single memory cell is limited to the size of the memory cell. If the value of the time difference (difference between consecutive cardiac time intervals) is so large that it cannot be stored within a preset number of bits of data, then the time interval itself is stored in two consecutive memory locations and is represented by two eight bits of data. However, if the value of the time difference is within the storage capacity of a single memory cell, then the time difference is stored in memory rather than the time interval data itself. As a result, storage space the memory is conserved since two consecutive memory locations are used to store the time interval data only when the value of the time difference is greater than the permissible storage capacity of one memory location.

The above and other objects and advantages will become more readily apparent when reference is made to the following description taken in conjunction when the accompanying drawings.

DETAILED DESCRIPTION OF THE DRAWINGS

Figure 1:
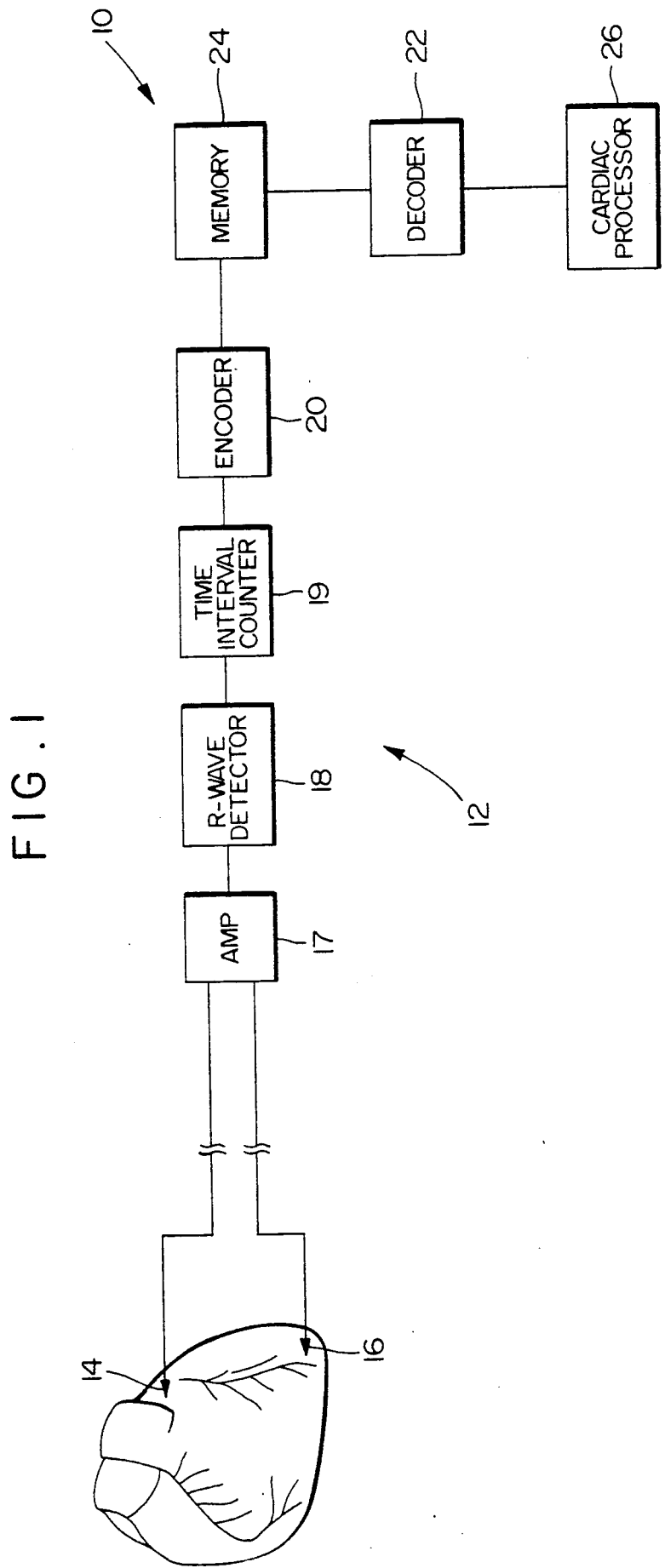
FIG. 1 is a block diagram illustrating the Holter function data encoding-decoding system according to the present invention as used in an implantable device.

Referring first to FIG. 1, the Holter function data encoding-decoding system of the present invention is generally shown at 10 as used in an implantable cardiac system 12. The Holter function data encoding-decoding system receives input data as time intervals representing cardiac cycle length. Specifically, sensing electrodes 14 and 16 are provided on or about the heart for picking up the electrical activity of the heart. These signals are then amplified by the amplifier 17. The signals are then input to an R-wave (or A-wave) detector 18 which triggers a time interval counter 19 to produce a series of time intervals which represent successive cardiac cycles lengths. The output of the time interval counter 19 is a 16 bit representation of the time interval of successive cardiac cycles.

The Holter function data encoding-decoding system comprises an encoder 20 and a decoder 22. The encoder 20 encodes the data from the time interval counter 19 for storage in the memory 24. The decoder 22 decodes the stored and encoded data in the memory 24 for processing by a cardiac processor 26.

The time interval measurements produced by the amplifier 17, detector 18, and time interval counter 19 provide the history of the cardiac cycle lengths over time. In an effort to increase the storage capacity of the memory 24, the encoder 20 is designed to encode the cardiac cycle length data so as to nearly double the storage capacity of the memory 24. In accordance with the detailed description of the encoding and decoding algorithms to follow hereinafter, the memory preferably stores 8 bits of data as one byte in a single storage location.

Figure 2:
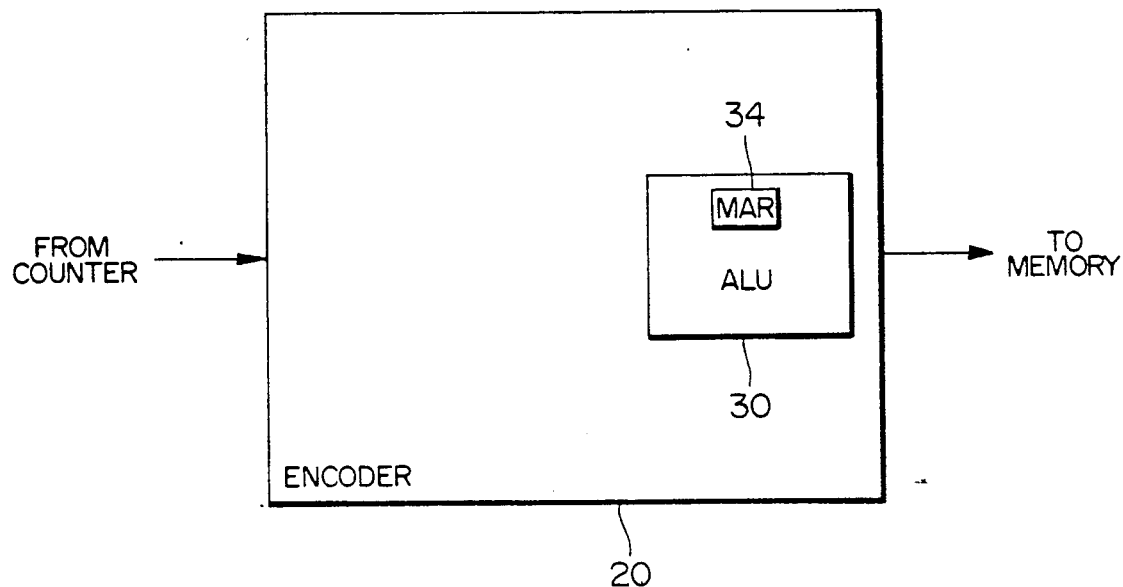
FIG. 2 is a block diagram illustrating the encoder portion of the Holter function data encoding-decoding system of the present invention.

FIG. 2 shows the components of the encoder 20 which comprises an ALU 30 having a memory address register (MAR) 34. The ALU 30 performs necessary mathematical functions to manipulate the time interval data for storing an encoded representation of the time interval data, intermixed with data representative of changes in the time interval, in the memory 24.

Figure 3:
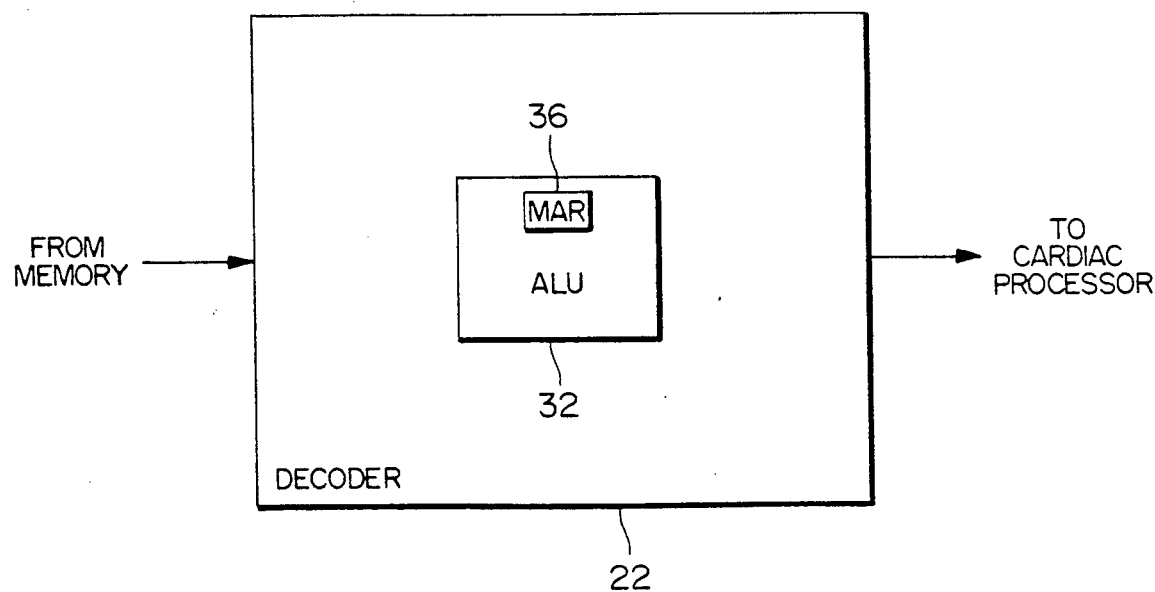
FIG. 3 is a block diagram illustrating the decoder portion of the Holter function data encoding-decoding system according to the present invention.

Similarly, the decoder 22 shown in FIG. 3 comprises an ALU 32 having a MAR 36 for decoding the encoded representation of the time interval data according for retrieving the actual time interval data. The ALU 32 also performs the necessary mathematical operations to recover the data encoded and stored in the memory 24.

Both the encoder 20 and the decoder 22 perform their respective encoding and decoding algorithms under the control of a computer program stored in a ROM (not shown) of each device. Specifically, the ALU's in the encoder 20 and the decoder 22 are controlled by the program to perform the necessary computations in the proper sequence and to control the MAR's in each device when accessing the memory 24 for storing or retrieving data. In this regard, the associated components which allow for the implementation of the computer program are not shown since it is well known in the art that computers and microprocessors include these components. The illustration of the ALU and MAR in FIGS. 2 and 3 are not intended to be exhaustive but are provided to more readily explain the operation of the encoding and decoding algorithms according to the present invention. Furthermore, the encoder 20 and decoder 22 interact with the memory 24 via a memory buffer register (MBR), not shown, much like that in conventional computers and microprocessors.

The thrust of the encoding algorithm is to compute the difference between consecutive values of cardiac time intervals and to store either the time interval or the difference depending on the magnitude of the difference. Specifically, each memory location in the memory is capable of storing a predetermined number of bits of data, for example, eight bits. If the magnitude of the time difference is so large that it cannot be represented by seven bits of data (8 bits less one bit used as a flag for indicating whether time difference of time interval data is stored), then the time interval itself is stored in two consecutive memory locations and is represented by two eight bits of data. However, if the magnitude of the time difference is not greater than what can be represented by an eight bit memory cell, then the time difference is stored in memory rather than the time interval data itself. As a result, storage space the memory is conserved since two consecutive memory locations are used to store the time interval data only when the value of the time difference is greater than the permissible storage capacity of one memory location.

For the first value of time interval data, there will be no previous value to be compare with. Therefore, upon beginning the encoding algorithm, the first two locations stored to will represent the first time interval. Subsequently, time interval data and time difference data may be interleaved in memory depending on the magnitude of the variation between consecutive values of time interval data. It is possible, therefore, for only the first two storage locations to hold time interval data whereas the remaining locations hold time difference data if the variation between consecutive cardiac cycles is within the storage capacity of a single memory location. Thus, the cardiac cycle time interval history is reconstructed during the decoding algorithm by sequentially computing the time interval of a cardiac cycle based on the previous time interval and the time interval difference stored in memory.

Figure 4:
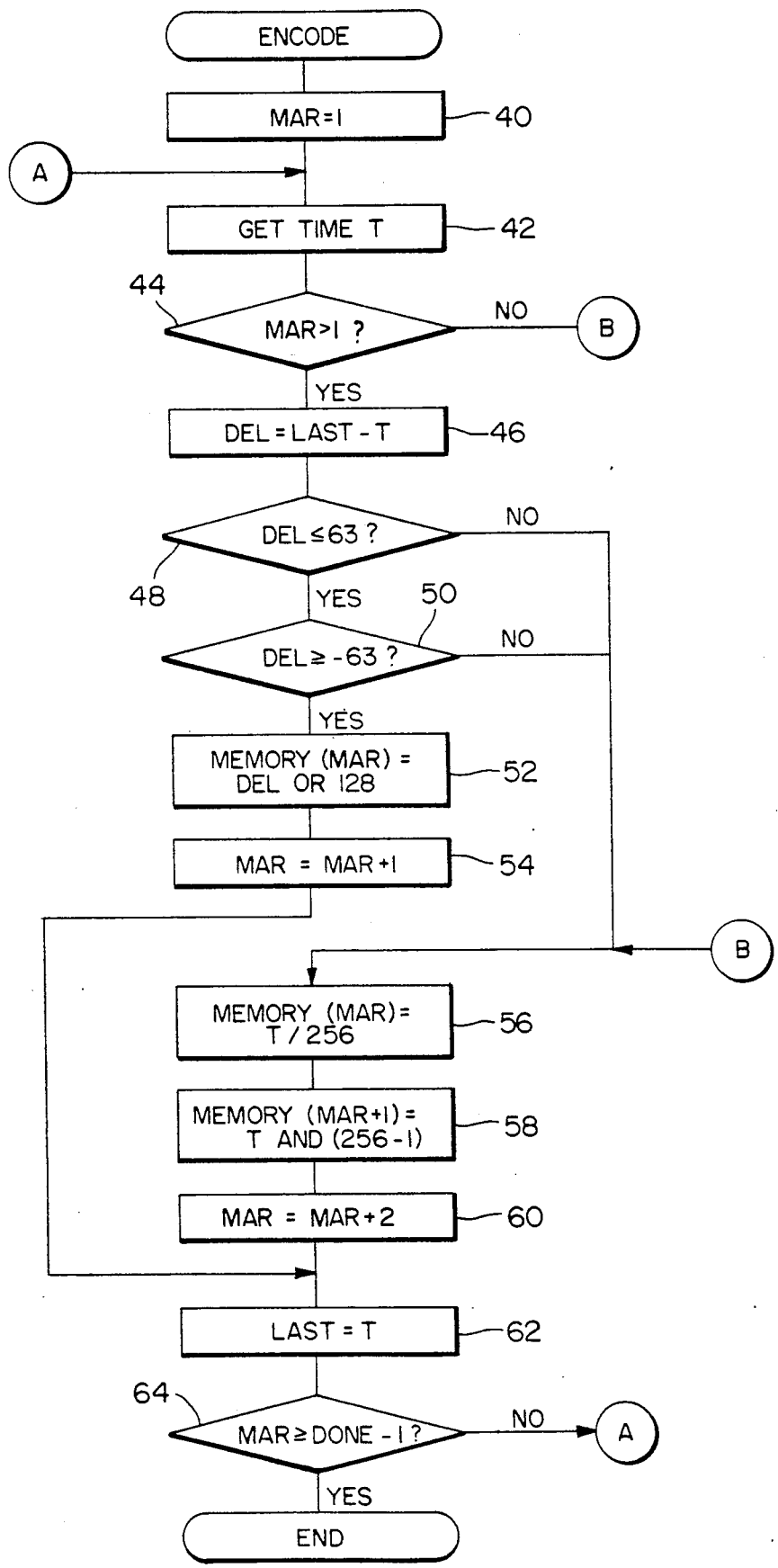
FIG. 4 is a flow diagram of the encoder shown in FIG. 2.

FIG. 4 illustrates the encoding algorithm in detail. As an initializing step 40, the MAR 34 of the encoder 20 is set to a starting value of 1. Subsequently, the current value of the cardiac cycle time interval (T) is obtained from the time interval counter 28 in step 42. Next, the value of the MAR 34 is examined in step 44. If the value of the MAR 34 is greater than 1, the algorithm continues to step 46 where the difference between the current time interval T and the previous time interval (LAST) is computed by the ALU 30 of the encoder and stored in a local RAM cell or other ALU register as the variable DEL.

As an example for understanding the present invention, the memory comprises memory locations which can store 8 bits of data as a single byte. The most significant bit of the byte is reserved for use as a flag to indicate whether time difference or time interval data is stored. The remaining bits are used to store the value of the data stored. Positive numbers between zero and $(2^6-1)$ 63 are stored in the conventional binary representation in the least significant seven bits. Negative numbers between zero and $-63$ ($-2^6-1$) are stored by taking the two's compliment of the binary representation of the corresponding positive number. Consequently, in the example chosen for explaining the present invention, each byte (8 bits) of memory can store a number less than positive 63 but greater than negative 63.

In step 48, a comparison is made between the value of the variable DEL with a preset value of 63. If the value of DEL is less than or equal to 63, then a second determination is made in step 50 for determining if DEL is greater than or equal to $-63$. Thus, steps 48 and 50 set the range for storing the value of DEL in one byte. Specifically, if the value of DEL is greater than or equal to $-63$ and less than or equal to 63, then the value of DEL is stored, in step 52, in one byte (8 bits) of memory space at the address according to the value of the MAR 34. The value of DEL stored in step 52 is provided with a flag by setting the most significant bit to 1 through a logical OR operation with the binary equivalent of the decimal number 128. As will become more apparent hereinafter, the step of setting the value of DEL negative when storing it in the memory serves as a tagging procedure so that, during the decoding routine, it can be recognized whether the data stored in a particular memory location is change in time interval data or time interval data. The MAR 34 is then incremented in step 54.

If the value of DEL is not less than or equal to 63 (step 48) or is not greater than or equal to $-63$ (step 50), then the encode algorithm does not implement steps 52 and 54, but jumps to steps 56 and 58. In steps 56 and 58, the 16 bit word representing the current interval T is separated into 2 bytes (an upper byte and a lower byte) by dividing the current interval T by the binary equivalent of the decimal number 256 to isolate the upper byte of the word which is stored in memory at the address of the current value of the MAR 34. In step 58, the lower byte of the word is isolated by a logical operation AND with a mask byte having all 8 bits set high as indicated by the expression "(256−1)" and is subsequently stored at the address of the current value of the MAR 34 plus 1. The MAR 34 is then incremented by 2 in step 60.

Should steps 52 and 54 be executed, under the condition that the value of DEL is inclusively between −63 and 63, then the algorithm jumps to step 62 and continues from there.

The time interval information is then updated in step 62 by storing the current time interval T as the previous time interval LAST. A check is then made of the MAR 34 in step 64. If the value of the MAR 34 is greater than or equal to a preset value DONE, less one, then the encode algorithm is terminated. Otherwise, the algorithm continues again from step 42. As is evident from the foregoing, the encoding algorithm processes the time interval data in sequence with its detection so that the data is stored in consecutive storage cells of the memory in time sequence with its occurrence.

The encode algorithm described above allows for free intermixing storage of the variables DEL and T in memory for each cycle, and based upon the logic of this routine, allows for reconstruction of the original cycle lengths from the stored data. For example, the above encoding method can be used to store 25 minutes of cardiac cycle length data with 1 millisecond resolution in 2048 (8 bit) bytes of memory if the average rate is 72 ppm and the PVC rate is 10 per minute.

Figure 6:
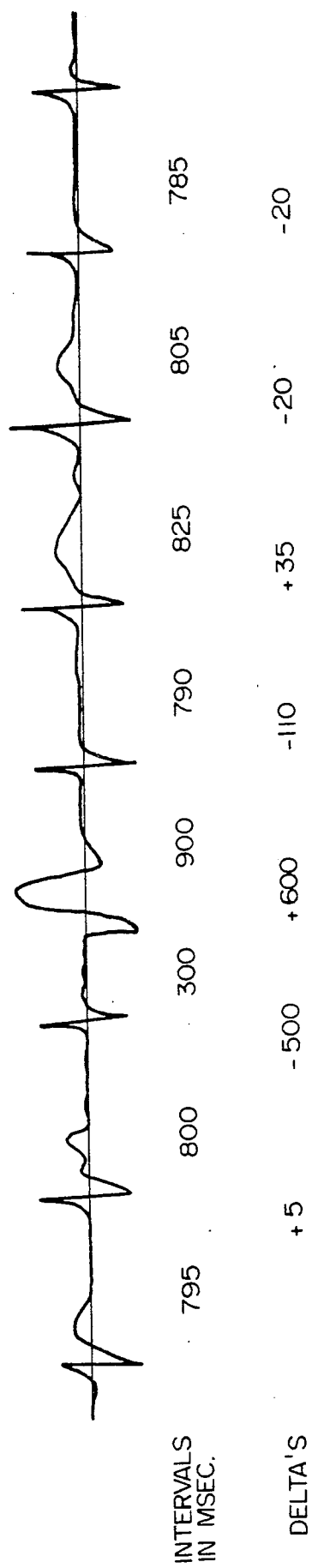
FIG. 6 is a diagram illustrating an example of cardiac data to be encoded according to the present invention.

FIG. 6 illustrates as an example cardiac time interval data for a cardiac signal. The time interval data of a cardiac cycle is represented in milliseconds as indicated in the figure. Table 1 set forth below lists the corresponding memory contents for the data shown in FIG. 6 as it would be stored after being processed by the encoding algorithm shown in FIG. 4 and described above. In this example, each memory location stores eight bits of data as a single byte. When the value of DEL is greater than 63 or less than −63 indicating that it cannot be stored in eight bits of data, the 16 bits of data representing the current value of the time interval is stored at consecutive addresses in the memory. For example, memory locations 02 and 03 store the 16 bit word (two bytes) required to represent 300 in consecutive memory locations. On the other hand, when the value of DEL is less than 63 or greater than −63 indicating that value of DEL can be stored in eight bits of data, the value of the DEL is stored in memory at the address according to the current value of the MAR 34. See, for example, memory location 01.

TABLE 1

| TIME INTERVALS | DEL | BINARY | HEXADEC | ADDRESS |
|---|---|---|---|---|
| 795 | ? | ? | ? | 00 |
| 800 | +5 | 1000 0101 | 85 | 01 |
| 300 | −500 | 0000 0001 | 01 | 02 |
|  |  | 0010 1100 | 2C | 03 |
| 900 | +600 | 0000 0011 | 03 | 04 |
|  |  | 1000 0100 | 84 | 05 |
| 790 | −110 | .0000 0011 | 03 | 06 |
|  |  | 0001 0110 | 16 | 07 |
| 825 | +35 | 1010 0011 | A3 | 08 |
| 805 | −20 | 1110 1100 | EC | 09 |

TABLE 1-continued

| TIME INTERVALS | DEL | BINARY | HEXADEC | ADDRESS |
|---|---|---|---|---|
| 785 | −20 | 1110 1100 | EC | 10 |

Figure 5:
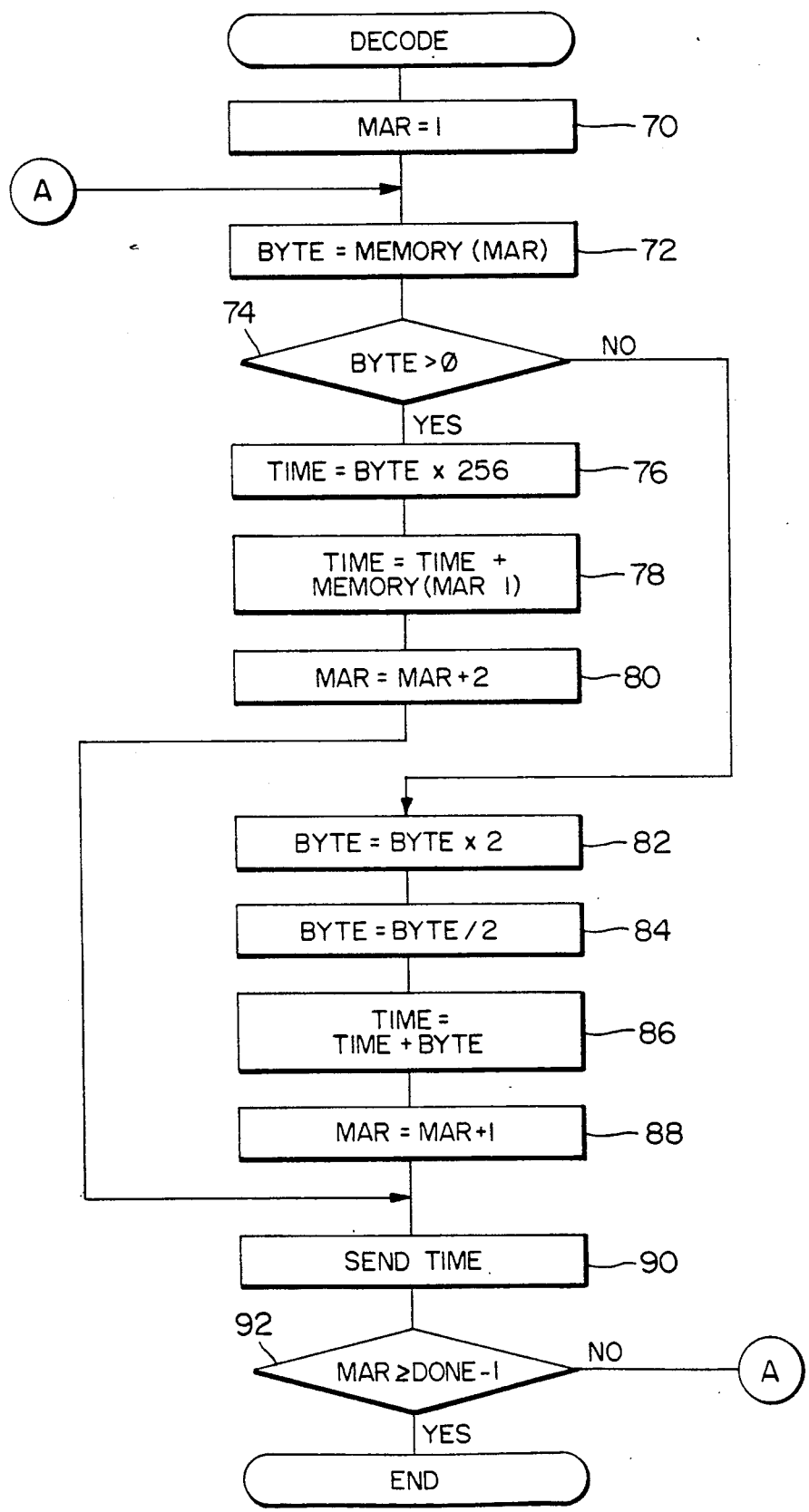
FIG. 5 is a flow diagram of the decoder shown in FIG. 3.

FIG. 5 illustrates the decoding algorithm performed by the decoder 22 in detail. In step 70, the MAR 36 of the decoder 22 is initialized to start decoding the stored data in the memory 24 from the first storage cell containing data. That is, the data is retrieved in a first-in-first-out (FIFO) manner to recover the cardiac cycle time interval data in the order in which is was stored for obtaining the proper time sequence of cardiac activity as it occurred and was detected. In step 72, the next byte of data from the memory is obtained at the address according to the value of the MAR 36. Next, the value of this byte of data is examined in step 74. Particularly, the most significant bit of the 8 bit data byte is examined. If the most significant bit of the byte of data is 0 (the 8 bit byte represents a number greater than zero), indicating that it is not the DEL variable stored at that particular location, the decoding procedure continues to steps 76 and 78 for recovering the 16 bit word representing the time interval data (2 bytes). In step 76, the upper byte of the word is retrieved from memory by multiplying the value of the byte at the memory address corresponding to the value of the MAR 36 by the binary equivalent of the decimal number 256. In step 78, the lower byte of the word is retrieved from memory at the address MAR+1 and is combined with the upper byte by addition. Thereafter, the value of the MAR 36 is incremented by 2 in step 80.

If the most significant bit of the 8 bit byte initially retrieved and examined in step 74 is 1 (the 8 bit byte represents a number less than zero) indicating that the data stored at that particular location is the DEL variable, the decoding procedure jumps to step 82. In steps 82-86, the value of the variable DEL is recovered. Initially, in step 84, the byte is shifted left to "end off" the upper or most significant bit. Then in step 84, the byte is shifted right with sign extension to recover the original DEL in the range −63 to +63. Next, in step 86, the value of DEL recovered is combined with the value of the last interval TIME (on the right side of the equation which is stored in a register in the ALU or other RAM cell) to find the current interval TIME (on the left side of the equation). The MAR 36 is then incremented in step 88.

After performing steps 80 and 88, the procedure continues to step 90 for sending the time interval data embodied in the variable TIME to the cardiac processor 26 for further analysis. Finally, in step 92 the value of the MAR 36 is checked to see if it is less than or equal to the preset value DONE less one. The decoding procedure, like the encoding procedure, continues until the value of the respective MAR equals the preset value DONE.

Referring to Table 1, an example of the progression of the decoding algorithm will now be explained. With the MAR 36 initialized, a fetch is made from the memory location corresponding to the initial value of the MAR. In this example, this corresponds to memory location 01. The data stored at this location in hexadecimal is 85 indicating that a negative number is stored at the location. Consequently, the most significant bit is ended off by a shift operation (step 82), and a right shift sign extension operation is then performed (step 84).

Thereafter, the current time interval is computed by adding the previous time interval 795 to the now computed value of DEL which is 5. On the other hand, if the value of the eight bits of data fetched from memory is greater than zero indicating that time interval data is to be directly retrieved from memory, then the upper eight bits of the timer interval data is first retrieved (step 76) and the upper eight bits is combined with the lower eight bits of the time interval data retrieved from the very next memory location.

The encoding and decoding algorithms described above provide for mixed storage of data indicative of cardiac cycle time intervals (T) and changes in the cardiac cycle time intervals (DEL). While the methods above have been described with respect to bytes of data comprising 8 bits, it is also possible to implement the same algorithms with nibbles (4 bits) of data.

The above description is intended by way of example only and is not intended to limit the present invention in any way except as set forth in the following claims.

We claim:

1. A method for encoding/decoding cardiac data for storage in a memory of a body implantable device, the method comprising the steps of:
   providing a memory having addresses and storage cells each having a corresponding address;
   detecting the cardiac electrical activity of the heart;
   determining the time interval of successive cardiac cycles from the detected electrical activity of the heart;
   encoding said cardiac data comprising the steps of:
   computing the time difference between the time intervals of successive cardiac cycles;
   determining if the time difference between the time intervals of successive cardiac cycles falls within a predetermined range;
   storing the value of the time difference in a particular storage cell of said memory at a corresponding particular address if said time difference falls within said predetermined range and setting the value of the stored time difference to be negative; and
   storing the time interval in two consecutive storage cells in said memory if said time difference does not fall within said predetermined range;
   decoding the stored cardiac data comprising the steps of:
   retrieving data in a storage cell at an initial address in said memory;
   determining if the value of the data at said initial address is greater than zero;
   retrieving said time interval at consecutive storage cells in said memory if said value of the data at said initial address is greater than zero; and
   retrieving said time difference if said value of data at said initial address is not greater than zero and computing said time interval by adding a previously retrieved time interval to the time difference.

2. The method of claim 1, and further comprising the steps of:
   generating a 16 bit binary representation of said time interval;
   providing each storage cell in said memory with 8 bits of storage space;
   and wherein said step of storing said time interval comprises the steps of:
   isolating the upper eight bits of said 16 bit binary representation and storing said upper eight bits in a first storage cell in said memory;
   isolating the lower eight bits of said 16 bit binary representation and storing said lower eight bits in a second storage cell having a memory address one greater than that of said first storage cell.

3. The method of claim 2, wherein said step of isolating the upper eight bits comprises the step of dividing said 16 bit binary representation by the binary equivalent of the decimal number 256, and wherein said step of isolating the lower eight bits of said 16 bit representation comprises the step of performing a logical AND operation with a mask byte comprises eight bits set high, and wherein said step of retrieving said time interval comprises the steps of:
   deriving said upper eight bits of said 16 bit representation by multiplying the data at said initial address by the binary equivalent of the decimal number 256; and
   retrieving from the storage cell at the memory address one greater than that of the initial address the lower eight bits of said 16 bit representation and adding said upper eight bits to said lower eight bits.

4. The method of claim 1, wherein said predetermined range is less than or equal to the decimal number 63 and greater than or equal to the decimal number −63, said predetermined range corresponding to the storage capacity of a single cell of memory.

5. A system for encoding/decoding cardiac data for storage in a memory implantable within the body comprising:
   cardiac detecting means for detecting the cardiac electrical activity of the heart;
   means for determining the time interval of successive cardiac cycles from the detected electrical activity of the heart;
   memory means for storing said cardiac data comprising a plurality of storage cells each associated with a corresponding memory address;
   encoding means for encoding said cardiac data comprising an encoding arithmetic logic unit and a encoding memory address register, said encoding arithmetic logic unit computing the time difference between time intervals of successive cardiac cycles and determining if the time difference between the time intervals of successive cardiac cycles falls within a predetermined range, said encoding means storing the value of the time difference in a particular storage cell of said memory corresponding to the value of said encoding memory address register if said time difference falls within said predetermined range and setting the value of the stored time difference to be negative, or storing the time interval in two consecutive storage cells in said memory if said time difference does not fall within said predetermined range; and
   decoding means for decoding the stored cardiac data comprising an decoding arithmetic logic unit and a decoding memory address register, said decoding means retrieving data in a storage cell at an initial address in said memory corresponding to an initial value of said memory address register, said decoding arithmetic logic unit determining if the value of the data at said initial address is greater than zero, said decoding means retrieving said time interval if said value of the data at said initial address is greater than zero at consecutive storage cells in said memory, or said decoding means retrieving said time difference if said value of data at said initial address is not greater than zero and said decoding arithmetic logic unit computing said time interval by adding a previously retrieved time interval to the time difference.

6. A method for encoding/decoding cardiac data for storage in a memory implantable within the body comprising the steps of:

providing a memory having addresses and storage cells each having a corresponding address;

detecting the cardiac electrical activity of the heart;

continuously determining the time interval of successive cardiac cycles from the detected electrical activity of the heart;

encoding said cardiac data comprising the steps of:
(a) setting a encoding memory address register to an initial value corresponding to an initial storage cell in said memory;
(b) computing the time difference between the time intervals of successive cardiac cycles;
(c) determining if the time difference between a time interval of a most current cardiac cycle and a time interval of a previous cardiac cycle falls within a predetermined range;
(d) storing the value of the time difference in said memory at an address corresponding to the value of said memory if said time difference falls within said predetermined range, setting the value of the stored time difference to be negative, and incrementing the encoding memory address register by one;
(e) storing the time interval of a most current cardiac cycle in said memory at consecutive addresses including an address corresponding to the value of said encoding memory address register and at an address corresponding to one greater than the value of said memory address register if said time difference does not fall within said predetermined range and incrementing the memory address register by two;
(f) temporarily storing the time interval of the most current cardiac cycle as the time interval of the previous cardiac cycle; and
(g) repeating encoding steps (b)-(f) until it is desired to terminate storage;

decoding the stored cardiac data comprising the steps of:
(h) setting a decoding memory address register to an initial value data corresponding to said initial address of said memory;
(i) fetching data from a storage cell of said memory according to the value of said decoding memory address register;
(j) determining if the value of the data fetched from said memory is greater than zero;
(k) retrieving the time interval of the most current cardiac cycle at consecutive storage cells in said memory if said value of the data at said initial address is greater than zero and incrementing said decoding memory address register by two; and
(l) retrieving said time difference if said value of data at said initial address is not greater than zero, computing said time interval of the most current cardiac cycle by adding the time interval of the previous cardiac cycle to the time difference, and incrementing said decoding memory address register by 1; and
(m) repeating steps (i)-(l) until all data is retrieved from said memory.

7. The method of claim 6, and further comprising the steps of:

continuously generating a 16 bit binary representation of said time interval;

providing each storage cell in said memory with 8 bits of storage space;

and wherein said step (e) of storing said time interval further comprises the steps of:

isolating the upper eight bits of said 16 bit binary representation and storing said upper eight bits in a storage cell at an address corresponding to the value of said encoding memory address register;

isolating the lower eight bits of said 16 bit binary representation and storing said lower eight bits in a storage cell at a memory address one greater than that of said lower eight bits.

8. The method of claim 7, wherein said step of isolating the upper eight bits comprises the step of dividing said 16 bit binary representation by the binary equivalent of the decimal number 256, and wherein said step of isolating the lower eight bits of said 16 bit representation comprises the step of performing a logical AND operation with a mask byte comprises eight bits set high, and wherein said step (k) of retrieving said time interval comprises the steps of:

deriving said upper eight bits of said 16 bit representation by multiplying the data in the storage cell corresponding to the value of said decoding memory address register by the binary equivalent of the decimal number 256; and fetching from the storage cell at the memory address one greater than that of decoding memory address register the lower eight bits of said 16 bit representation and adding said upper eight tits to said lower eight bits.

9. The method of claim 6, wherein said predetermined range is less than or equal to the decimal number 63 and greater than or equal to the decimal number −63.

10. A method for encoding cardiac data for storage in a memory in an implantable device, the method comprising the steps of:

providing a memory having addresses and storage cells each having a corresponding address;

sensing the electrical activity of the heart;

determining the time intervals of successive cardiac cycles;

determining the change in the time intervals between successive cardiac cycles;

determining if the time difference between the time intervals of successive cardiac cycles falls within a predetermined range;

storing the value of the time difference in a particular storage cell of said memory at a corresponding particular address if said time difference falls within said predetermined range and setting the value of the stored time difference to be negative; and storing the time interval in two consecutive storage cells in said memory if said time difference does not fall within said predetermined range.

11. The method of claim 10, and further comprising the steps of:

generating a 16 bit binary representation of said time interval;

providing each storage cell in said memory with 8 bits of storage space;

and wherein said step of storing said time interval comprises the steps of:

isolating the upper eight bits of said 16 bit binary representation and storing said upper eight bits in a first storage cell in said memory;

isolating the lower eight bits of said 16 bit binary representation and storing said lower eight bits in a second storage cell having a memory address one greater than that of said first storage cell.

12. The method of claim 11, wherein said step of isolating the upper eight bits comprises the step of dividing said 16 bit binary representation by the binary equivalent of the decimal number 256, and wherein said step of isolating the lower eight bits of said 16 bit representation comprises the step of performing a logical AND operation with a mask byte comprises eight bits set high.

13. A method for encoding cardiac data for storage in a memory in an implantable device, the method comprising the steps of:

(a) providing a memory having addresses and storage cells each having a corresponding address;

(b) detecting the cardiac electrical activity of the heart;

(c) continuously determining the time interval of successive cardiac cycles from the detected electrical activity of the heart;

(d) continuously computing the time difference between the time intervals of successive cardiac cycles;

(e) setting a encoding memory address register to an initial value corresponding to an initial storage cell in said memory;

(f) determining if the time difference between a time interval of a most current cardiac cycle and a time interval of a previous cardiac cycle falls within a predetermined range;

(g) storing the value of the time difference in said memory at an address corresponding to the value of said memory if said time difference falls within said predetermined range, setting the value of the stored time difference to be negative, and incrementing the encoding memory address register by one;

(h) storing the time interval of a most current cardiac cycle in said memory at consecutive addresses including an address corresponding to the value of said encoding memory address register and at an address corresponding to one greater than the value of said memory address register if said time difference does not fall within said predetermined range and incrementing the memory address register by two;

(i) temporarily storing the time interval of the most current cardiac cycle as the time interval of the previous cardiac cycle; and (j) repeating encoding steps (f)-(i) until it is desired to terminate storage;

14. The method of claim 13, and further comprising the steps of:

continuously generating a 16 bit binary representation of said time interval;

providing each storage cell in said memory with 8 bits of storage space;

and wherein said step (h) of storing said time interval further comprises the steps of:

isolating the upper eight bits of said 16 bit binary representation and storing said upper eight bits in a storage cell at an address corresponding to the value of said encoding memory address register;

isolating the lower eight bits of said 16 bit binary representation and storing said lower eight bits in a storage cell at a memory address one greater than that of said lower eight bits.

15. The method of claim 14, wherein said step of isolating the upper eight bits comprises the step of dividing said 16 bit binary representation by the binary equivalent of the decimal number 256, and wherein said step of isolating the lower eight bits of said 16 bit representation comprises the step of performing a logical AND operation with a mask byte comprises eight bits set high.

16. In a method for detecting and storing cardiac data in a memory of a body implantable device comprising detecting the electrical activity of the heart, determining the time interval of the cardiac cycle of the heart, the improvement comprising a method for encoding said cardiac data for storage in said memory comprising the steps of:

determining the change in the time intervals between successive cardiac cycles;

determining if the time difference between the time intervals of successive cardiac cycles falls within a predetermined range;

storing the value of the time difference in a particular storage cell of said memory at a corresponding particular address if said time difference falls within said predetermined range and setting the value of the stored time difference to be negative; and storing the time interval in two consecutive storage cells in said memory if said time difference does not fall within said predetermined range.

17. In a method for detecting and storing cardiac data in a memory of a body implantable device comprising detecting the electrical activity of the heart, determining the time interval of the cardiac cycle of the heart, the improvement comprising a method for encoding said cardiac data for storage in said memory comprising the steps of:

computing the change in the time intervals of successive cardiac cycles; and storing the time interval or the change in time intervals sequentially in the memory depending upon the value of the change in the time intervals of successive cardiac cycles.

18. A method for encoding/decoding cardiac data for storage in a memory of a body implantable device, the method comprising the steps of:

detecting the electrical activity of the heart;

determining the time interval of the cardiac cycle of the heart;

encoding said cardiac data for storage in said memory comprising the steps of:

continuously computing the change in the time intervals of successive cardiac cycles; and continuously storing the time interval or the change in time intervals sequentially in storage cells of the memory depending upon the value of the change in the time intervals of successive cardiac cycles; and providing a tag on the stored data representing change in time interval upon storing said time interval in said memory;

fetching data from said memory;

decoding the data retrieved from said memory comprising the steps of:

examining the contents of said data retrieved from said memory;

determining if said data retrieved from said memory is time interval or change in time interval data on the basis of the presence or absence of said tag associated with said data retrieved from said memory;

computing the time interval upon the presence of said tag by adding a previously retrieved time interval to said change in time interval; and designating said data retrieved from said memory as said time interval data upon the absence of said tag.

19. In a method for detecting and storing cardiac data in a memory of a body implantable device comprising detecting the electrical activity of the heart, determining the time interval of the cardiac cycle of the heart, the improvement comprising a method for encoding said cardiac data for storage in said memory comprising the steps of:

determining the change in the time intervals between successive cardiac cycles;

determining if the magnitude of the time difference between the time intervals of successive cardiac cycles is within a storage capacity of a single memory cell in the memory;

storing the value of the time difference in a particular storage cell of said memory at a corresponding particular address if said time difference is within the storage capacity of a single memory cell providing a flag on stored time difference; and storing the time interval in two consecutive storage cells in said memory if said time difference is not within the storage capacity of a single memory cell.

* * * * *